United States Patent
Pond

(10) Patent No.: US 6,808,511 B2
(45) Date of Patent: Oct. 26, 2004

(54) DISPOSABLE ASPIRATING SAFETY SYRINGE

(76) Inventor: Gary J. Pond, 2816 N. Main St., Racine, WI (US) 53402

(*) Notice: Subject to any disclaimer, the term of this patent is extended or adjusted under 35 U.S.C. 154(b) by 0 days.

(21) Appl. No.: 09/976,682

(22) Filed: Oct. 11, 2001

(65) Prior Publication Data

US 2003/0073958 A1 Apr. 17, 2003

(51) Int. Cl.[7] ............................................. A61M 5/32
(52) U.S. Cl. ........................ 604/192; 604/205; 604/232
(58) Field of Search ............................... 604/192–203, 604/205, 232, 234, 235, 187, 218, 221, 222, 227, 228–229, 231, 236, 246, 244, 245

(56) References Cited

U.S. PATENT DOCUMENTS

| | | | | |
|---|---|---|---|---|
| 3,556,099 A | * | 1/1971 | Knight | 128/218 |
| 5,217,436 A | * | 6/1993 | Farkas | 604/110 |
| 5,330,440 A | * | 7/1994 | Stanners et al. | 604/195 |
| 5,370,619 A | * | 12/1994 | Rossi | 604/110 |
| 5,380,286 A | * | 1/1995 | van den Haak | 604/110 |
| 5,395,345 A | | 3/1995 | Gross | |
| 5,445,620 A | * | 8/1995 | Haber et al. | 604/232 |
| 5,472,431 A | | 12/1995 | Godat et al. | |
| 5,582,595 A | | 12/1996 | Haber et al. | |
| 5,814,023 A | | 9/1998 | Fulk et al. | |
| 5,830,152 A | | 11/1998 | Tao | |
| 5,931,813 A | * | 8/1999 | Liu | 604/110 |
| 5,964,735 A | | 10/1999 | Alexander | |
| 6,068,616 A | * | 5/2000 | Janus | 604/240 |
| 6,210,369 B1 | * | 4/2001 | Wilmot et al. | 604/157 |
| 6,231,550 B1 | | 5/2001 | Laughlin | |
| RE37,439 E | * | 11/2001 | Firth et al. | 604/110 |

* cited by examiner

Primary Examiner—Christopher L. Chin
Assistant Examiner—Ann Y. Lam
(74) Attorney, Agent, or Firm—Ryan Kromholz & Manion, S.C.

(57) ABSTRACT

A disposable aspirating syringe for dental medicine having the ability to accept single use or disposable drug cartridges. The syringe offers a retractable needle and a break-away plunger to facilitate disposal and increase safety.

15 Claims, 10 Drawing Sheets

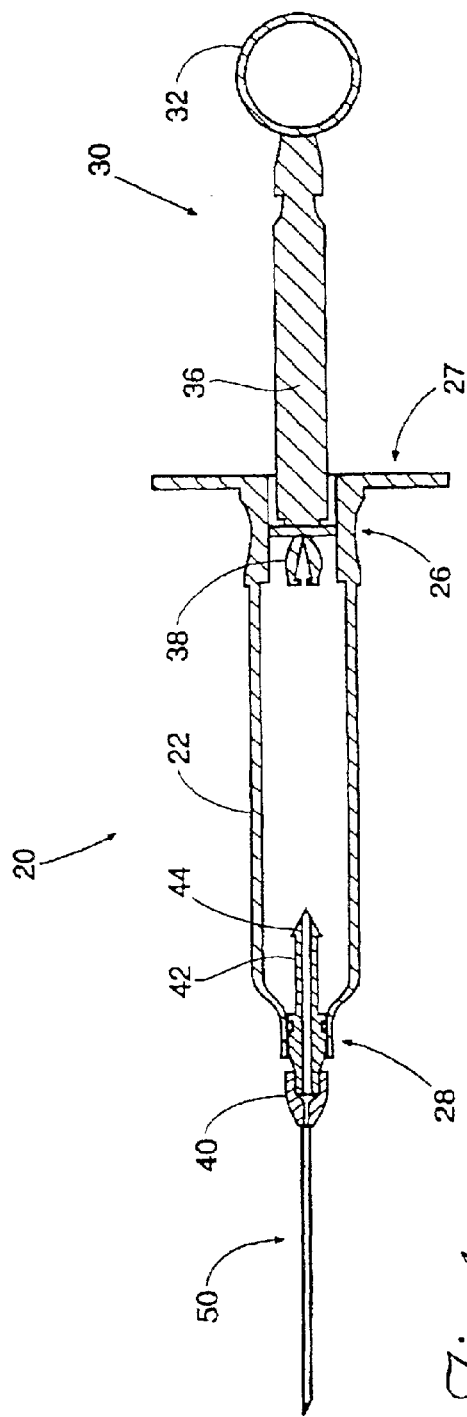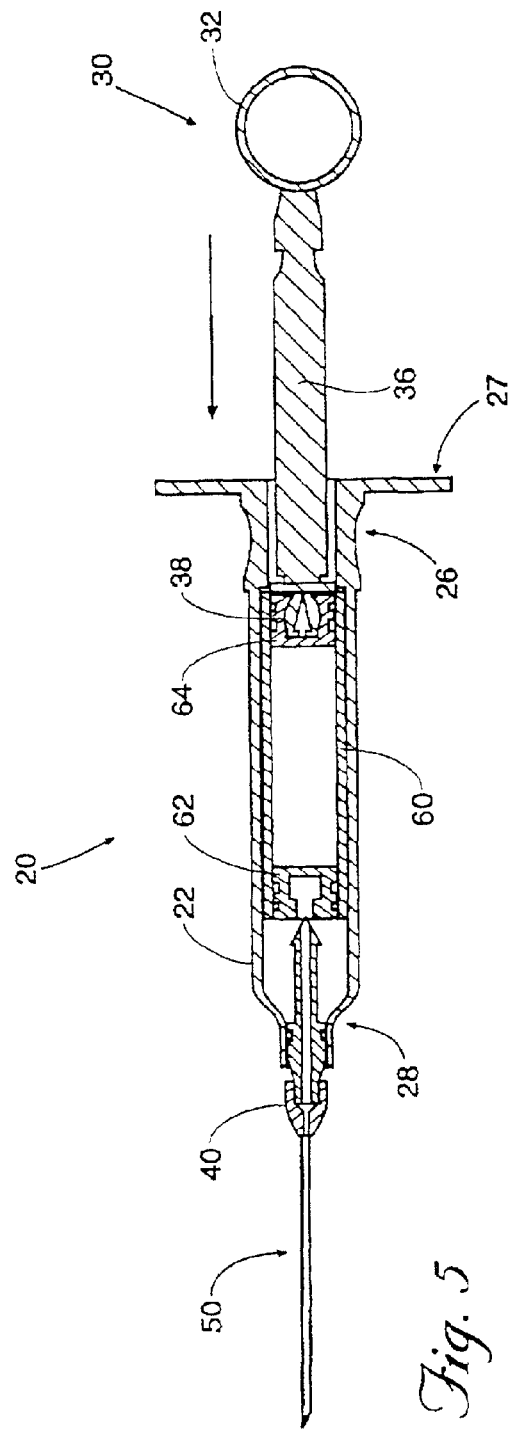
Fig. 4
Fig. 5

DISPOSABLE ASPIRATING SAFETY SYRINGE

BACKGROUND OF THE INVENTION

This invention relates to non-reusable aspirating safety syringes with retractable needles for use, for example, in the dental, medical or veterinary arts.

Disposable syringes with retractable needles are desirable because they are economical and hygienic. Retractable needles are especially desirable because they greatly reduce accidental sticking of needles in caregivers and patients. Further, the retractable nature of needles is desirable because they provide a visual aid indicating prior use. In addition, many retractable designs make reuse of the needle and syringe impossible.

Of particular importance in the dental arts is a syringe that may be used to aspirate. Aspiration is the practice of retracting a syringe plunger in order to draw fluids from the patient's body into the drug cartridge so that the caregiver may verify whether a vein was mistakenly invaded. The desirable characteristics of aspirating syringes and other necessary functions are extolled in U.S. Pat. No. 6,068,618 and incorporated herein by reference.

However, in the dental arts, for example, medication and anesthetic are often consumed in disposable vials or cartridges. The prior art describes re-usable syringes that are adapted to receive such single use, disposable cartridges. But, there are inherent drawbacks to this method of consuming dental drugs.

First, traditional disposable syringes are generally inexpensive and simple in design. Further, some can retract a needle after use, thus facilitating proper disposal. But, they cannot accommodate common single use disposable drug cartridges.

To overcome some of these drawbacks, a re-usable syringe was developed. Constructed of a durable material, such as chrome plated brass or stainless steel, such syringes readily accepted the disposable cartridges and the syringes were adapted for use as aspirating syringes—having a modified plunger with a handle feature that facilitated both dispensing drugs and aspiration. Although this type of syringe is very successful, it too has drawbacks. For example, the durable construction from brass or stainless steel is costly. Second, the re-use of the syringe necessitates a relatively expensive sterilization procedure and additional equipment. Further, the re-useable syringe is susceptible to re-use prior to proper sterilization, which may promote the spread of germs, viruses and other contagious diseases.

In addition, the avoidance of needle sticks (that is the in advertent pricking of a patient or caregiver with a needle) when using re-useable syringe assemblies is not adequately addressed in the prior art, because many of such previous devices do not have the ability to retract a needle after use. In the current designs of most re-usable syringe assemblies, the needle must be removed by hand. This greatly increases the risk of an accidental needle stick.

It is therefore desirable to have a novel disposable syringe that incorporates the advantages of an economical syringe and the safety features of a retractable needle, with such characteristics as captured in reusable syringes, such as the ability to aspirate and accommodate disposable cartridges.

SUMMARY OF THE INVENTION

Generally, the novel syringe features a retractable needle. The syringe includes a plunger, a barrel and a body. The body is, for example, generally tubular and hollow and has a longitudinal opening. On the exterior of the body at a proximal end, there is a finger grip feature, which is known in the art. This feature is for the comfort and convenience of the caregiver, and the syringe would work in substantially the same manner with or without such a contoured finger grip. The syringe body may also include a handle at the proximal end. This feature could assist with aspiration and control of the syringe. At the oppositely spaced distal end of the body is a nozzle feature. The nozzle feature is adapted to receive the barrel assembly.

As mentioned, the body has a longitudinal opening. The longitudinal opening easily accepts a disposable cartridge of fluid drug, as known in the art. However, a cartridge may be successfully introduced to the syringe body by placing the cartridge in either a proximal or distal open end, in the alternative.

In lieu of a known cartridge, an alternative novel capsule may be used, as described subsequently. In either instance, the cartridge or the novel capsule may be inserted in the longitudinal opening, or introduced at one open end of the body. Once positioned, the cartridge or capsule is engaged by the plunger at one end and the barrel at a second end, for example. The barrel is adapted to pierce a flexible membrane or diaphragm of the capsule or cartridge.

The barrel has a feature that protrudes from a central body. The protrusion has a barb. The barb and protrusion are hollow, allowing fluid communication between the capsule or cartridge and the barrel assembly.

At an end opposite from the barbed protrusion is a threaded member, for example, that is adapted to receive a needle assembly, as known in the art. It is contemplated and within the scope of the present invention for the needle assembly to attach with a LUER® lock or any other locking mechanism. The needle assembly may be a double piercing needle, as typically used with re-useable syringe assemblies of the prior art. Alternatively, the needle assembly may be a single piercing construction as is common with known disposable, single use needles.

Also included with the barrel is a seal. The seal rests around a peripheral surface and is in sealing contact with the nozzle of the syringe body. For example, an o-ring may be used to removably seal the barrel and the body.

The nozzle of the syringe body has a feature that retains the barrel in fixed position, preventing the barrel from being dislodged from the distal end, but permitting the barrel and needle assemblies to be retracted after use and withdrawn toward the plunger end of the syringe body, and drawn entirely within the capsule.

The syringe assembly also has a plunger that is slidebly received in the hollow tubular body. The plunger has a feature that engages the top plug of the drug cartridge or capsule. The plunger may also include a looped member, as is used in the art to facilitate the use of the needle to aspirate. The plunger also has a breakaway feature, for example, a score line, so that a used plunger may be fractured after use. This will allow a more compact disposal of the invention.

As mentioned, a known disposable fluid drug cartridge may be used with this novel syringe. In such a case, a double piercing needle may be attached to the barrel assembly. One end of the needle would pass through the barrel and the barbed protrusion would pierce the cartridge diaphragm. After use, the double piercing needle would be unscrewed from the barrel. Then the syringe assembly and cartridge would be discarded normally. Alternately, a single piercing needle may be used. It would be attached to the barrel assembly. After use, the entire barrel along with the needle would be withdrawn and captured entirely within the capsule.

Therefore, the present invention alleviates many of the aforementioned deficiencies in the prior art. Insodoing, it is therefore one object of the invention to provide an aspirating safety syringe with a retractable needle. Moreover, it is an object of the present invention to provide a disposable aspirating syringe.

It is a further object of the invention to provide a syringe that can receive disposable, single use drug cartridges.

It is another object to provide such a disposable syringe that is economical to manufacture and dispose.

Another object of the invention is to increase safety by providing a visual means to indicate that a syringe has been used and also to reduce the probability of inadvertent needle "sticks."

Yet another object of the invention is to provide a novel disposable cartridge for drugs that can be used with the novel disposable aspirating syringe.

DESCRIPTION OF THE DRAWINGS

FIG. 4 is a sectional view of a syringe assembly showing the needle attached thereto and the plunger in a fully extended position.

FIG. 5 is a sectional view of a syringe assembly showing a capsule inserted therein and the plunger engaging the capsule.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Like parts are numbered alike in all figures.

Figure 1:
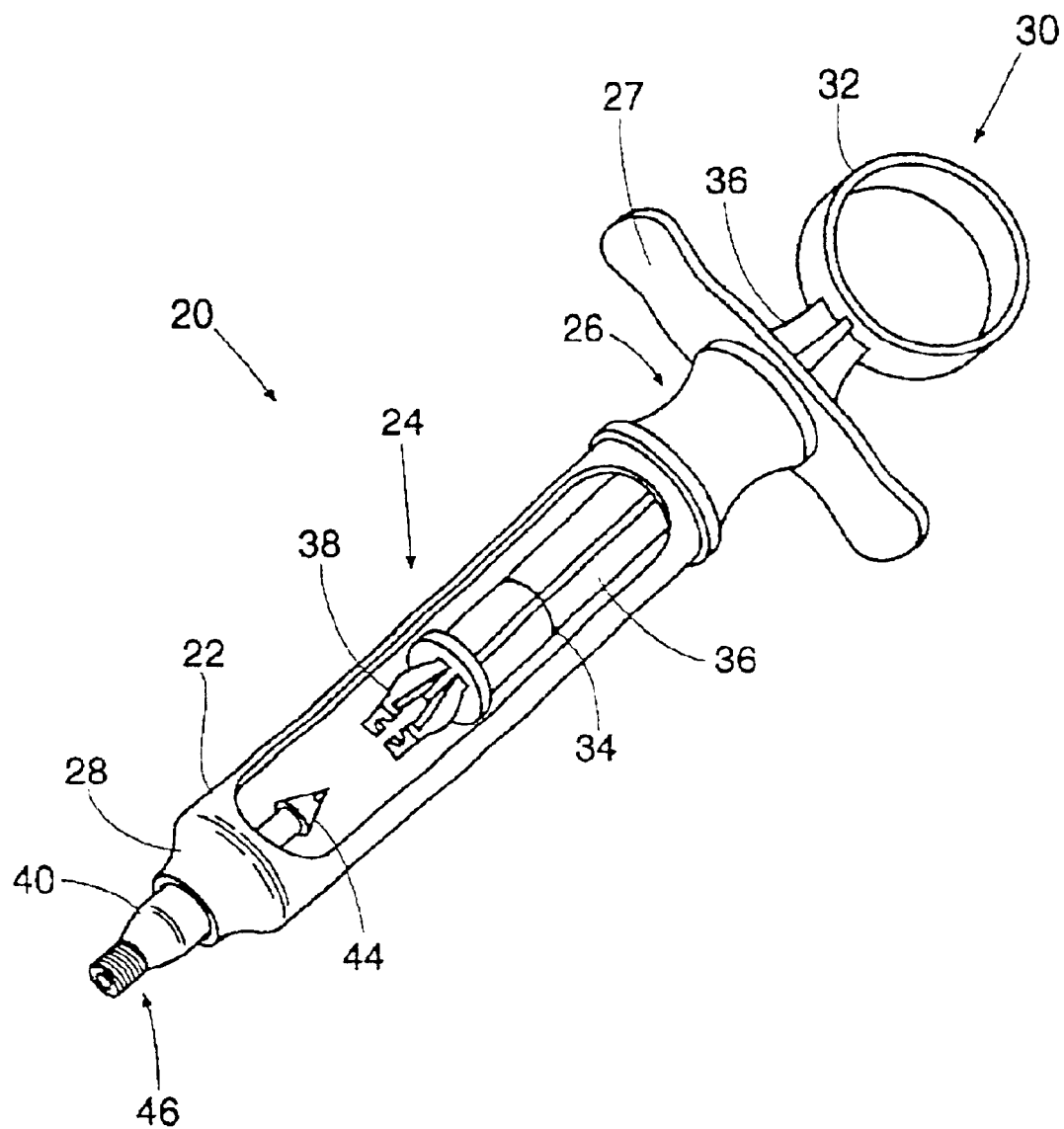
FIG. 1 is a perspective view of a novel aspirating disposable syringe with plunger in a collapsed position.

Referring now to the drawings, specifically FIG. 1, the syringe assembly 20 of the present invention is shown in a preferred embodiment. The syringe body 22 has a longitudinal opening 24, which is adapted to receive a single use drug cartridge (discussed subsequently). At one end of the body 22 the syringe 20 tapers to a nozzle 28, extending from the nozzle 28 is a portion of the barrel 40 namely, the threaded member 46. At an opposite end of the body 22, there is, for example, a contoured feature for a finger grip 26. Adjacent to the grip 26, a handle 27 may be included. Inserted in the body 22 is a plunger 30. The plunger may have a looped member 32 to facilitate aspiration, for example. The plunger 30 has a slender shaft 36 that connects the looped member 32 to an opposite spaced grippers 38. The shaft 36 may have a score line 34, which would facilitate breaking of the shaft 36 to aid disposal. The grippers 38 are adapted to be inserted in the capsule 60 (not shown in this figure, discussed subsequently). In FIG. 1, the syringe 20 is shown in a partially extended position, emulating the condition prior to use.

Figure 2:
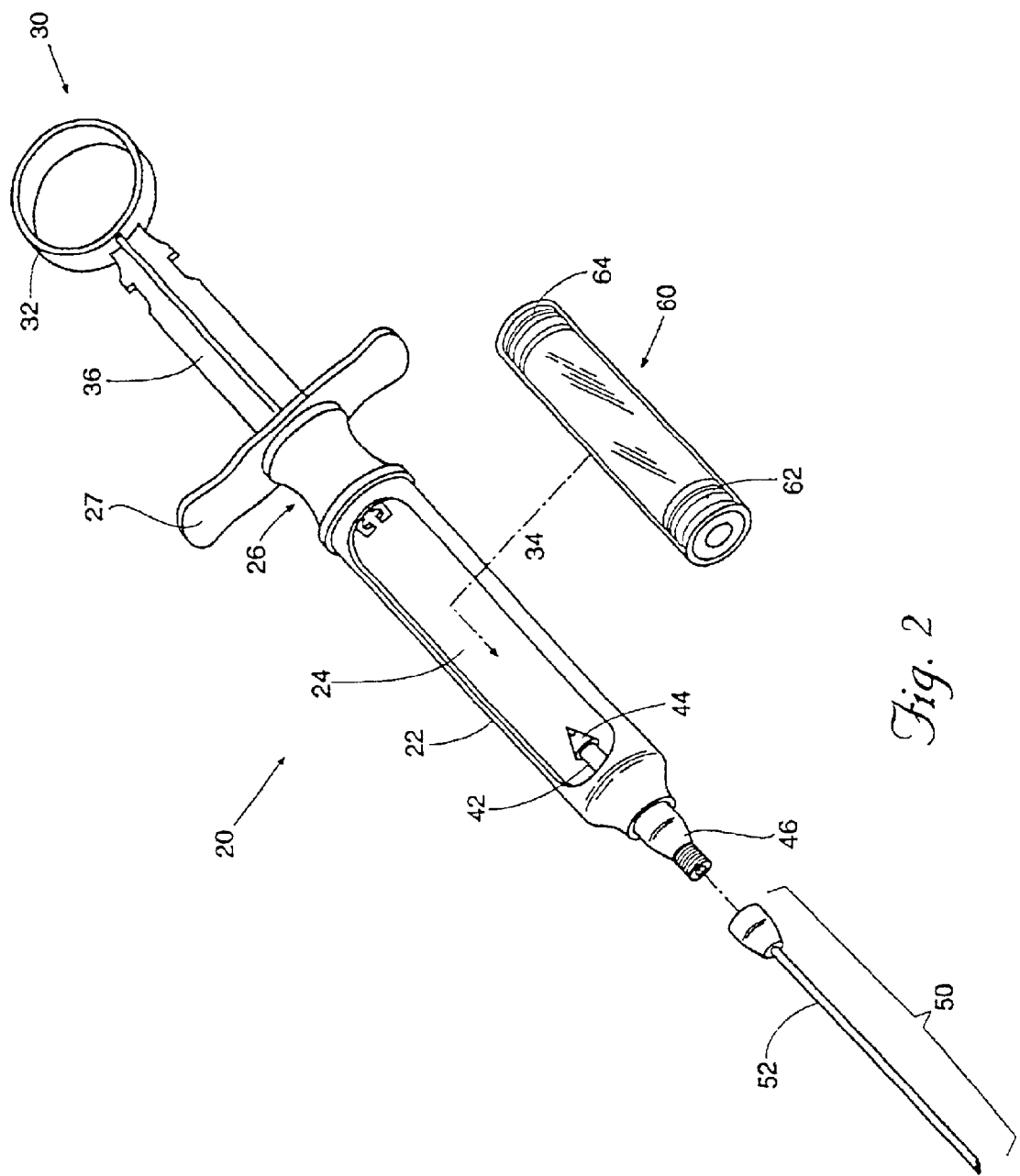
FIG. 2 is a perspective view of an aspirating disposable syringe showing, in assembly format, the relation of a single use drug cartridge and needle assembly thereto.

Referring now to FIG. 2, the syringe assembly 20 of the present invention is shown in relationship to an attachable needle 50 and an insertable capsule 60. The capsule 60 may be, for example, of the single use disposable type cartridge of the prior art or, alternatively, a novel capsule 60 (discussed subsequently). The cartridge or capsule 60 may be inserted through the longitudinal opening 24 of the syringe body 22, for example. The capsule may have a diaphragm 62 that seals one end of the capsule 60 and may be pierced by barb 44 of the barrel 40. At an opposite end of the capsule 60 there is a plug 64 that seals the capsule 60. The plug 64 permits the grippers 38 of the plunger 30 to invade, while maintaining the seal with the capsule 60. The plug 64 and diaphragm 62 may be unique in geometry, or, alternatively, they may be of the same geometry, albeit separate parts. In a preferred embodiment the diaphragm 62 and plug 64 are molded from a rubber or similar synthetic compound, as generally known in the art, and share similar geometry, for example.

In one embodiment, as shown in FIG. 2, a means for inserting the capsule 60 in a syringe assembly 20 may include, for example, a longitudinal opening 24. However, the cartridge may be introduced, alternately, for example, through the proximal open end of the body 22.

Still referring to FIG. 2, also shown is a needle assembly 50. Depicted in FIG. 2 is a single piercing needle 52 as is commonly known in the art. However, a double piercing needle 58 (see FIG. 11) could work just as well and in a similar manner. The needle 50 is attached to the barrel 40. The needle 50 may be, for example, screwed on to the threaded member 46 of the barrel 40. Alternatively, a common bayonet type fastening means, such as a LUER® lock mechanism, as known in the art, may be used to couple the needle to the barrel (not shown). Also visible in FIG. 2 is the barb 44 on the end of the protrusion 42, which are part of the barrel (partially hidden from view).

Again referring to FIG. 2, the plunger 30 is shown in a fully retracted or withdrawn position. In this position, the syringe assembly 20 is ready to receive a single use disposable drug cartridge (not shown) or capsule 60.

Figure 3:
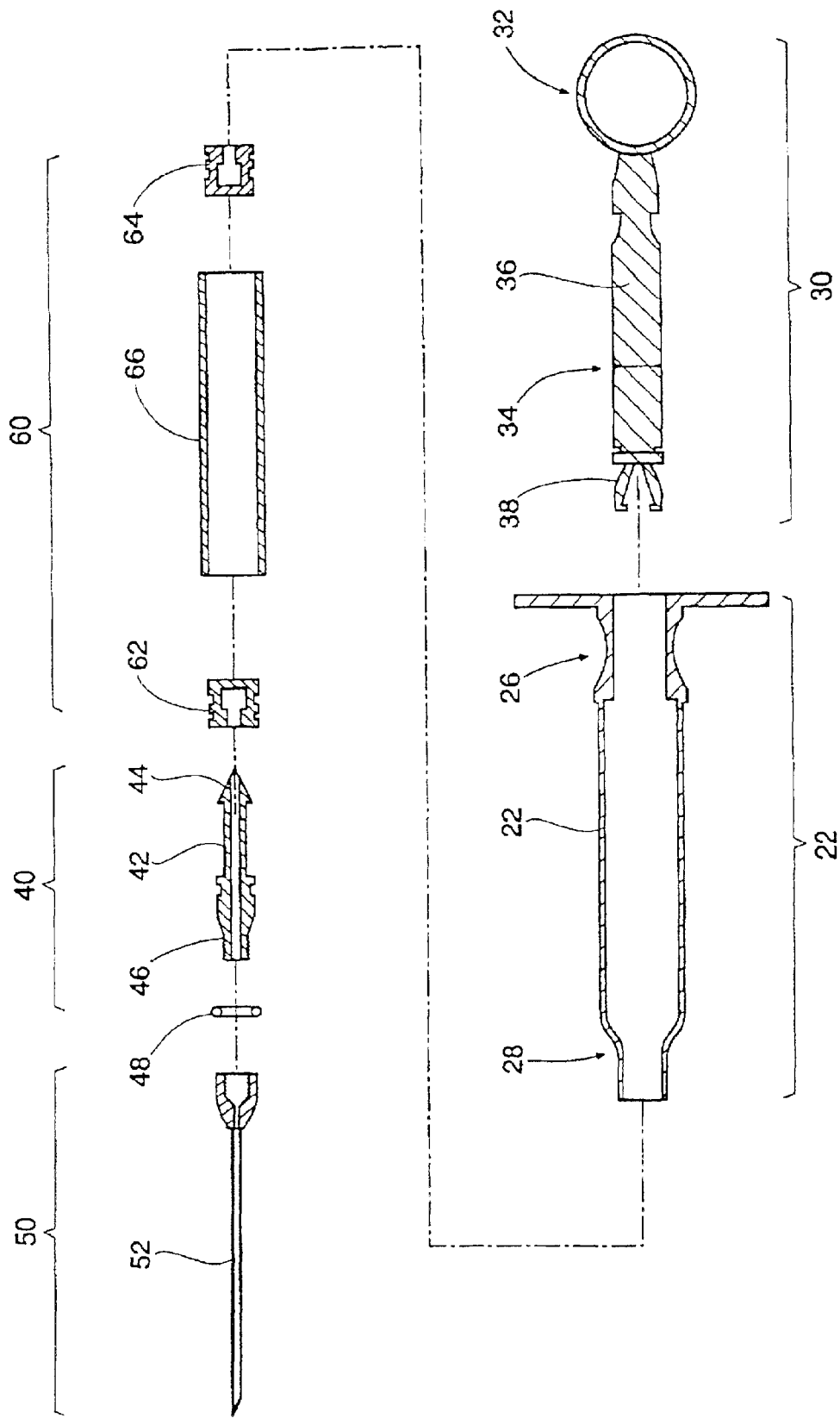
FIG. 3 is a sectional view, taken along the longitudinal axis of a syringe assembly and its components are shown in an exploded assembly view, the components of the assembly comprise a needle assembly, a barrel with protruding barb, an exploded capsule assembly, a syringe body and a plunger

Now referring to FIG. 3, an exploded view of a longitudinal cross section of the various components and assemblies that comprise a preferred embodiment of the present invention is shown. A needle assembly 50, shown here as a single piercing needle 52 attaches to the threaded member 46 of the barrel 40. Prior to attaching the needle 50 to the barrel 40, the barrel 40 may, preferably, be inserted into the nozzle portion 28 of the syringe body 22. The barrel 40 rests inside the body 22 at the nozzle 28 so that the threaded member 46 of the barrel 40 extends outside the syringe body 22. To seal and assist in retention of the barrel 40 within the nozzle 28, a sealing member 48, such as an o-ring, may be located on a peripheral feature of the barrel 40.

Still referring to FIG. 3, it is understood that the plunger 30 may be preferably inserted in the syringe body 22 prior to use. In one embodiment, the plunger may be pre-assembled to the body 22 at a remote manufacturing facility, for example. The plunger 30 slideably engages the interior of the body 22. At one end of the plunger 30 there is a looped member 32, as depicted in FIG. 3. The looped member 32 may assist the user in performing aspiration, as commonly used in the art of dental medicine. Alternative handle like features may be used with similar results. The looped member 32 is coupled to a shaft 36, which is adapted to slide within the interior of the syringe body 22. At an end opposite the handle 32 and also coupled to the common shaft 36 is a gripper 38. The gripper 38 is adapted to engage a feature on the capsule 60 (discussed subsequently).

Located in a predetermined position on the shaft is a line of weakness, called a score line 34. This line 34 is included on the shaft 36 to create a stress concentrating area so that the shaft 36 will fail in a predetermined position given a predetermined applied force. In a preferred embodiment the force required to break the shaft 36 at the score line 34 is that of an average caregiver's hand strength. The score line 34 is intended to assist the caregiver or user of the syringe in disposing of a used syringe assembly 20. Thus, the ordinary caregiver or user may simply break the shaft 36 at the score line 34 and easily discard the spent syringe. It will be understood that by breaking the plunger 30 from a syringe body 22 will reduce the amount of space required for disposal. However, the score line 34 is not essential to the performance of the syringe 20.

In addition, the plunger 30 may include a biasing means (not shown). It is understood that such a device may be used to enable the plunger 30 to self-aspirate.

Still referring to FIG. 3, a capsule 60 is shown having a plug 64 and a diaphragm 62. The plug 64 is adapted to receive the aforementioned gripper 38 of the plunger 30. The gripper 38 penetrates an outer surface of the plug 64. With the gripper 38 embedded in the plug 64, the plug 64 becomes coupled to the gripper 38. Thus, when the plunger 30 is depressed, the plug 64 is forced to travel in the direction of the plunger 30. Accordingly, if the plunger 30 reverses its direction of travel, the plug 64 will reverse as well, which provides the aspirating feature of this invention.

It should be noted that a preferred embodiment of the aspirating syringe 20 uses a novel capsule 60. However, existing drug cartridges for single use, as known in the art would work as well. Instead of the gripper 38 engaging a plug 64, the gripper 38 simply pushes on the stopper (not shown) of prior art cartridges (not shown).

Again referring to FIG. 3, a preferred embodiment shows a plug 64 and a diaphragm 62. The diaphragm 62 and the plug 64 both may, preferably, seal the capsule 60. Also, the diaphragm 62 is adapted to be pierced by either a prior art needle, such as a double piercing needle 58 (see FIG. 11), or by the barb 44 on the protrusion 42 of the barrel 40. Thus, it may be desirable to form, by a molding process, for example, the plug 64 and diaphragm 62 from the same material and in substantially the same geometry.

Referring now to FIGS. 4–8 inclusive, a sequence of operations may be observed demonstrating a preferred use of the present invention. FIG. 4 represents the syringe assembly 20 in a state that is ready for introduction of a single use drug capsule 60 or prior art disposable drug cartridge. The plunger 30 is fully retracted. The barrel 40 is installed in the nozzle 28 and a needle 50 is attached to the protruding threaded member 46 (hidden from view). In this sequence of figures, the needle 50 shown is a single piercing needle 52. However, a double piercing needle 58 (see FIG. 11) would operated in substantially the same manner.

A capsule 60 is inserted via the longitudinal opening 24 (not shown) on the syringe body 22. FIG. 5 depicts the engagement of the plunger 30 to the capsule 60. The gripper 38 at one end of the shaft 36 of the plunger 30 has penetrated the plug 64 of the capsule 60. Note the relative displacement of the plunger 30 assembly to the body 22. At the opposite end of the capsule 60, the barb 44 at the end of the protrusion 42 of the barrel 40 has not yet penetrated the diaphragm 62.

Figure 6:
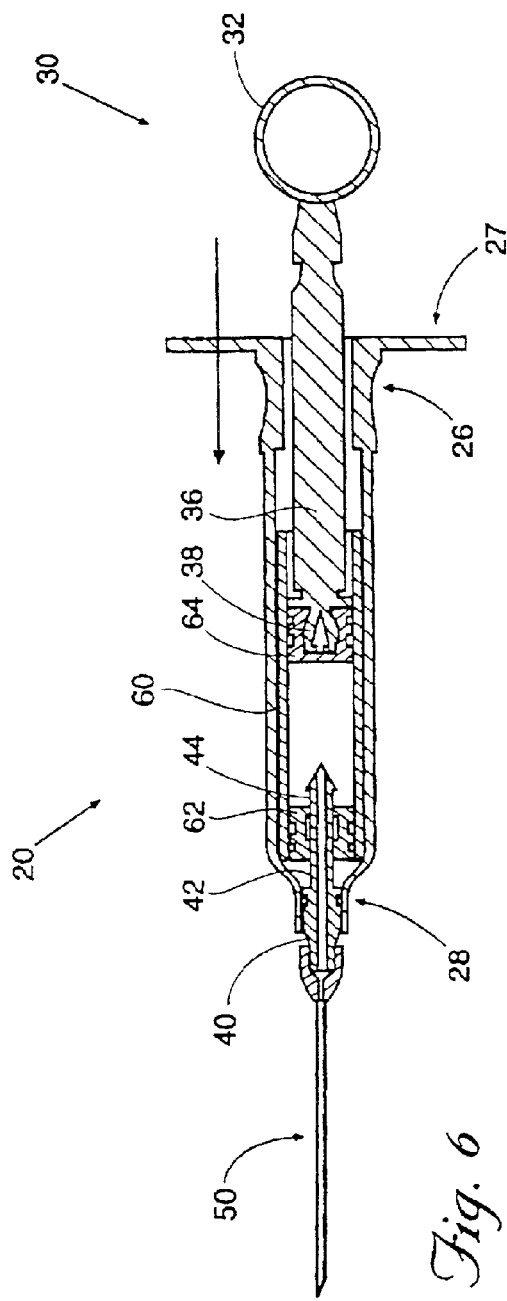
FIG. 6 is a sectional view of a syringe assembly with the plunger partially compressed and the capsule has been penetrated by the protruding barb of the barrel assembly.

Next, the diaphragm 62 is pierced by the barb 44, as shown in FIG. 6. The barb 44 is forced through the diaphragm 62 so that the barb 44 is in fluid communication with the drug contained inside the capsule 60.

As the plunger 30 continues to travel toward the body 22, the capsule 60 remains in fixed position, while the plug 64 moves with the plunger 30. In this manner, fluid is forced from the interior of the capsule 30 through the hollow interior of the barb 44 and protrusion 42. Thus, the barrel 40 acts as a conduit for the fluid from the capsule 60 to the needle assembly 50.

Figure 7:
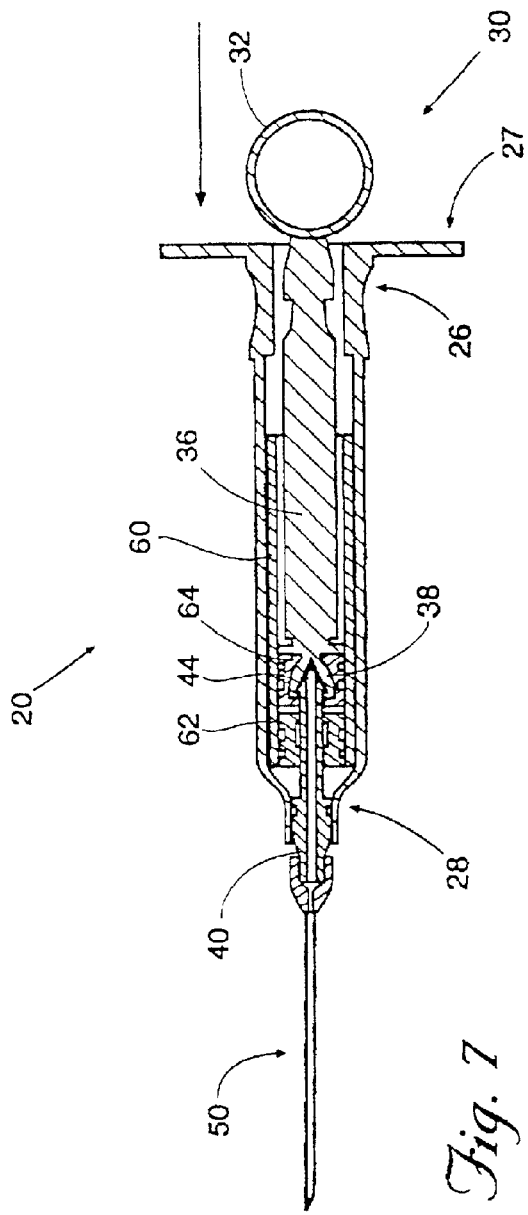
FIG. 7 is a sectional view of a syringe assembly with the plunger mostly compressed and engaging the barbed protrusion of the barrel assembly.

As FIG. 7 shows, when the plug 64 travels to a fully entrenched position in the capsule 60, the barb 44 is forced through the plug 64 and is captured by the gripper 38 of the plunger 30 in a manner that is understood in the art.

Figure 8:
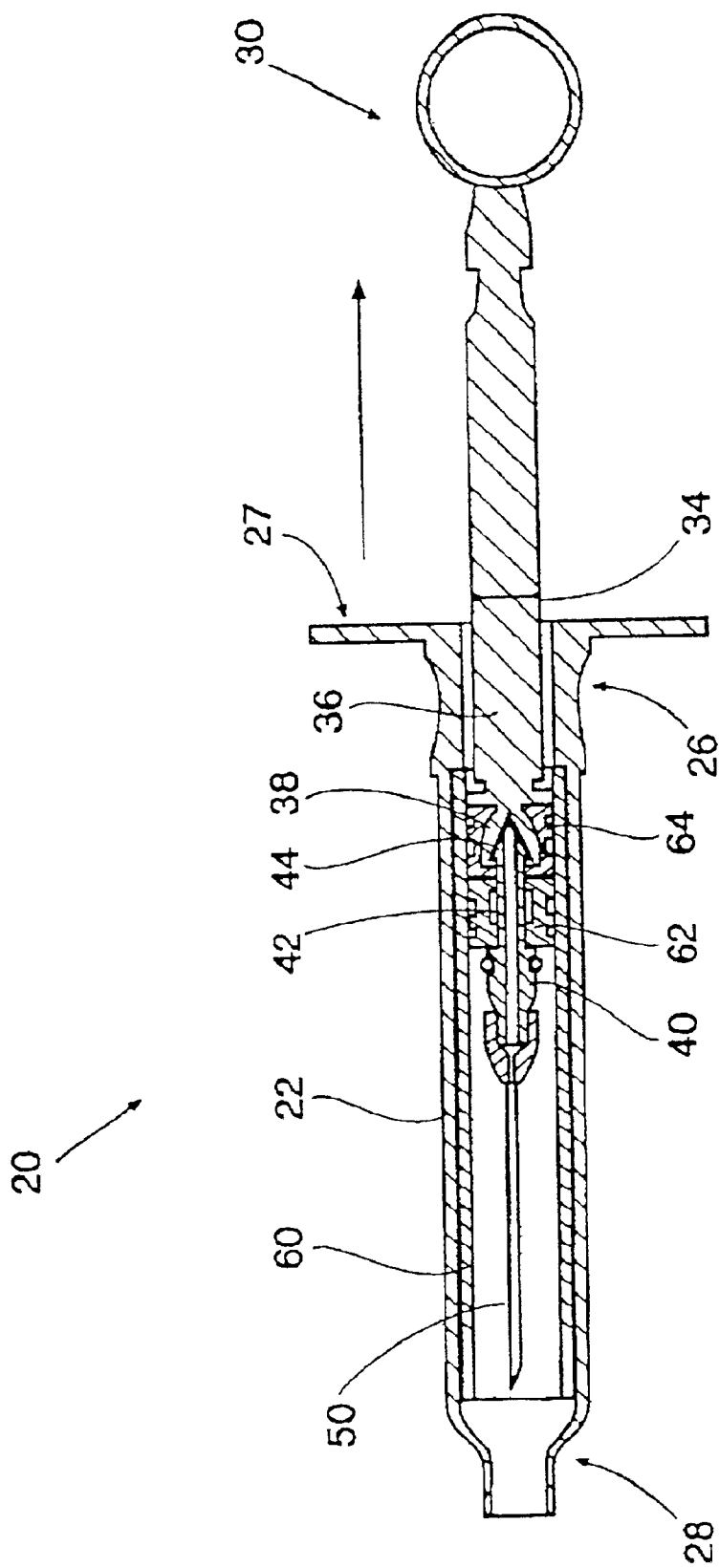
FIG. 8 is a sectional view of a syringe assembly with the plunger in the extended position after use. The needle assembly is retracted and contained wholly within the capsule.

Accordingly, as FIG. 8 shows, as the plunger 30 is retracted after use, the plug 64 and diaphragm 62 are brought along. Further, since the gripper 38 is coupled to the barb 44, the entire barrel 40 retracts along with the needle 50. When the plunger 30 is fully retracted, the needle 50 rests inside the capsule 60. At this point the syringe 20 may be discarded in a safe manner. Alternatively, the plunger 30 may be intentionally broken at the score line 34, thus two pieces may be discarded in a more compact format.

Figure 9:
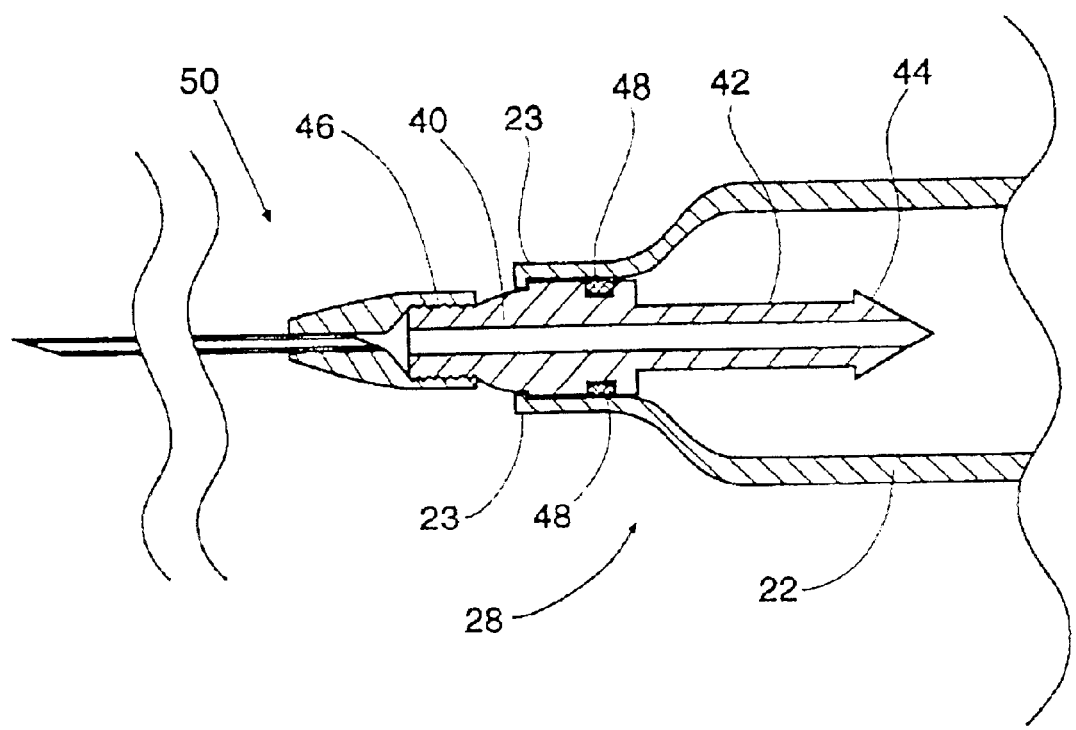
FIG. 9 is a detailed sectional view of the nozzle region of the syringe body depicting the retention of the barrel therein including the sealing member.

FIG. 9 highlights an embodiment of the syringe body 22. In order to prevent the barrel 40 from escaping from the end of the nozzle 28 in an undesirable direction, a retaining flange 23 is included. The flange 23 is dimensioned so to freely pass the threaded member 46 of the barrel and needle 50 through an aperture of the nozzle 28 when it is desired to retract the needle 50. Accordingly, the barrel 40 is adapted to use the flange 23.

FIG. 9 also highlights the hollow interior of the barrel 40, along with the fluid communication passage that connects the barb 44, the protrusion 42 and the needle assembly 50.

Figure 10:
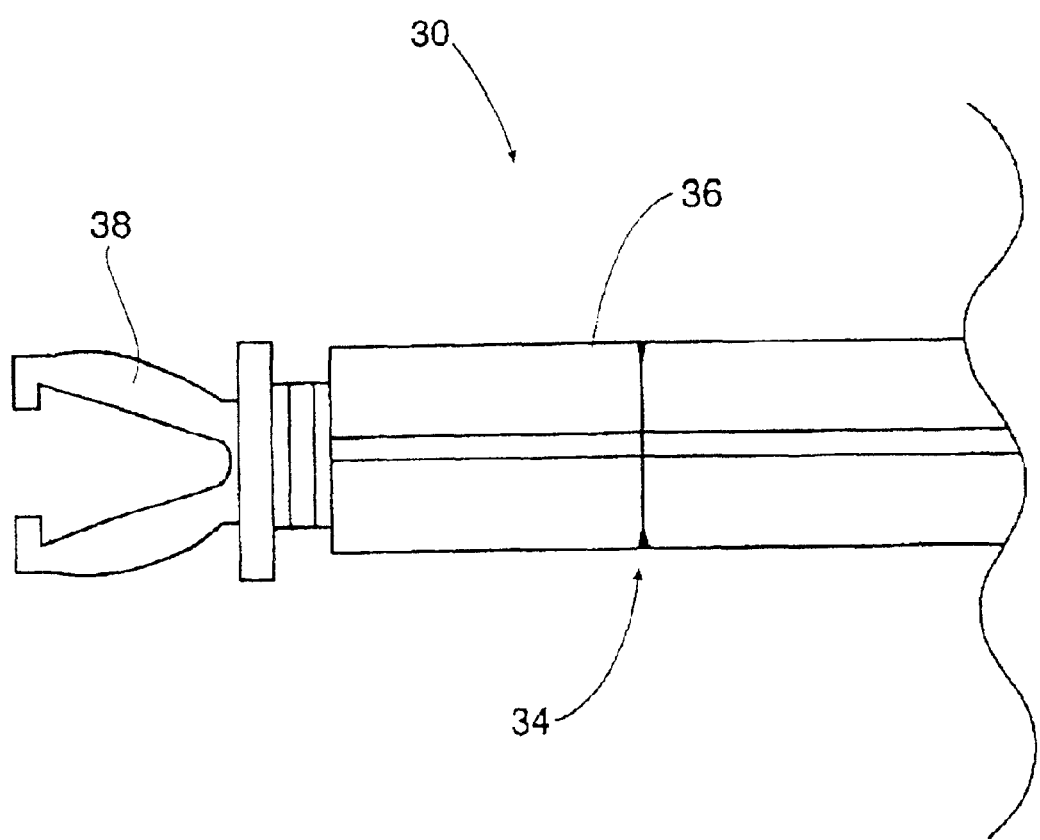
FIG. 10 is a detailed profile view of the plunger showing a score line.

FIG. 10 highlights, in a detail view, the score line 34 on the shaft 36 of the plunger 30.

Figure 11:
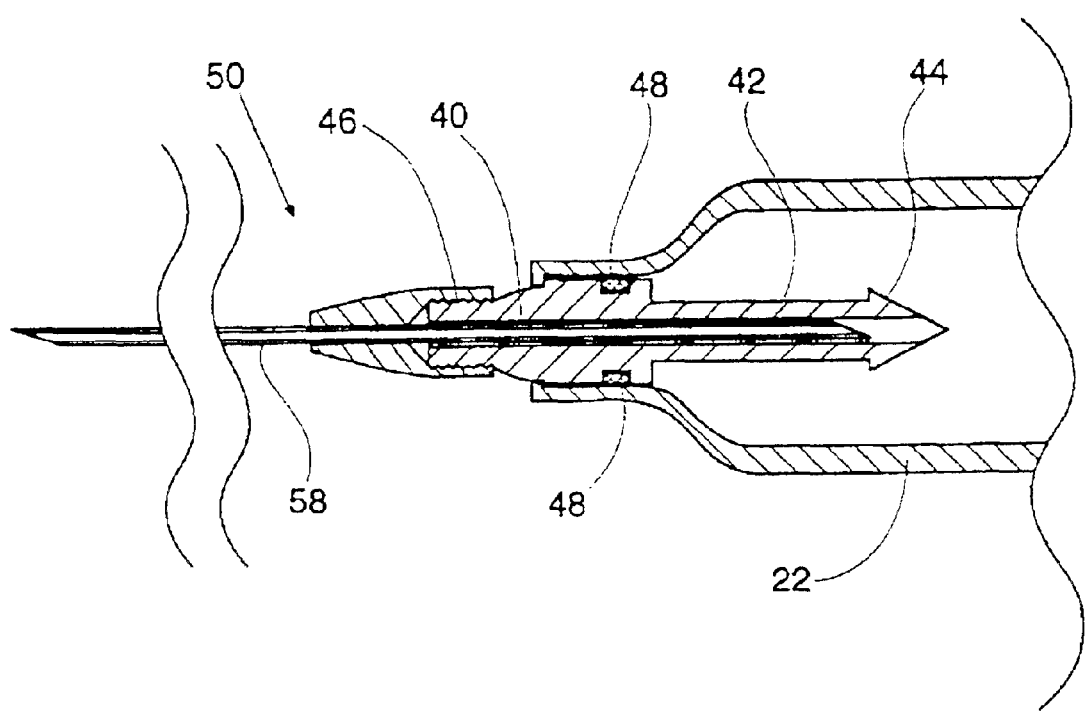
FIG. 11 is a detailed profile view of the barrel adapted for a double piercing needle.

FIG. 11 depicts an envisioned embodiment that uses a known double piercing needle 58. The double piercing needle 58 would be a part of the needle 50 which fastens to the barrel 40. A means of fastening may include, for example, mating threads on the needle 50 and the threaded member 46 of the barrel 40. The double piercing needle 58 may extend, for example, through a portion of the protrusion 42. Alternately, the needle 58 may extend beyond the barb 44 (not shown).

Figure 12:
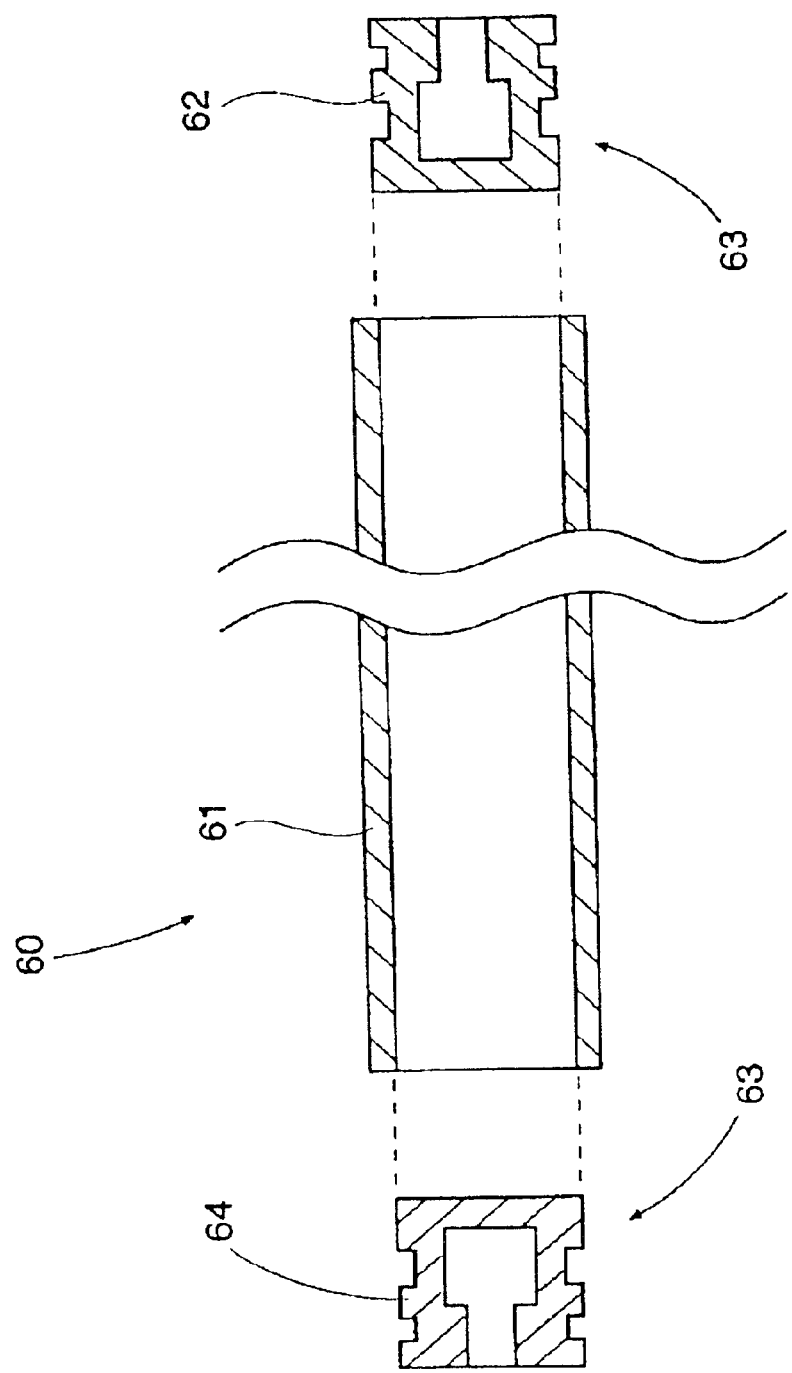
FIG. 12 is cross section of the capsule showing, in assembly format, the plug and plunger sealing means.

FIG. 12 shows a novel capsule 60 for a fluid, such as a drug or anesthetic. Single use cartridges, also called disposable cartridges or capsules, are contemplated. Such a capsule 60 is generally a hollow tubular body 61 and may be constructed from glass for example or what is commonly known as plexi-glass. The tube 61 has two oppositely spaced open ends. Each end having a flexible sealing member 63 that provides a hermetic seal with the tube walls, thus preventing the escape of any fluid. At one end, the sealing member 63 may consist of a diaphragm 62 which would have the additional characteristic of being piercable by either a double piercing needle 58 (see FIG. 11), or by a barb 44 (see FIGS. 1–8) as previously disclosed herein. At a second end, the sealing member 63 may consist of a plug 64, which would be adapted to receive a plunger 30 (FIGS. 1–8) as previously described, or by a plunger as is known in the prior art.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A syringe for use with a cartridge containing a liquid, the cartridge having a hollow body and being closed at one end with a piercable diaphragm and being closed at a second end with a plug, said diaphragm and said plug both creating a hermetic seal with said hollow body, the syringe comprising:
    a syringe body having a hollow interior, an open proximal end and an oppositely spaced open distal end;
    a plunger slidably received within the syringe body at the proximal end;
    a barrel slidably received in the hollow interior at the distal end of the syringe body, said barrel having an open end, said open end being positioned opposite a protrusion, said protrusion to pierce the diaphragm of the cartridge;
    a hollow needle coupled to the open end of the barrel;
    said needle having its innermost end axially spaced from said protrusion; and
    wherein said syringe body includes means for receiving the cartridge, said means comprising an elongated, exposed, longitudinal slot extending coaxially relative to and inwardly of the syringe body, said slot being located between the open proximal end and the oppositely spaced open distal end of said syringe body.

2. A syringe as claimed in claim 1 wherein the plunger further comprises a means for providing a breakaway feature intermediate the ends of said plunger.

3. The syringe as claimed in claim 2 wherein the means for providing a breakaway feature includes a peripherally scored groove located intermediate the ends of said plunger.

4. A syringe assembly as claimed in claim 1 wherein the syringe body further comprises a finger rest and a handle adjacent to said finger rest, said finger rest being located adjacent to the proximal end of said syringe body.

5. A syringe assembly as claimed in claim 1 wherein the plunger further comprises a looped manually operated member.

6. A syringe for use with a cartridge containing a liquid, the cartridge having a hollow body and being closed at one end with a piercable diaphragm and being closed at a second end with a plug, said diaphragm and said plug both creating a hermetic seal with said hollow body, the syringe comprising:
    a syringe body having a hollow interior, an open proximal end and an oppositely spaced open distal end, and means for receiving the cartridge, said cartridge receiving means comprising an elongated, exposed, longitudinal slot extending coaxially relative to and inwardly of the syringe body, said slot being located between the open proximal end and the oppositely spaced open distal end of said syringe body;
    a plunger slidably received within the syringe body at the proximal end;
    a barrel slidably received in the hollow interior at the distal end of the syringe body, said barrel having an open end, said open end being positioned opposite a protrusion, said protrusion to pierce the diaphragm of the cartridge; and
    a hollow needle coupled to the open end of the barrel;
    means for retracting the needle inside the syringe body, said needle retracting means comprising:
    a barbed member carried by the protrusion, said protrusion and said barbed member having concentric hollow interiors; and
    wherein said barrel further comprises a concentric bore and distal aperture, said bore and aperture being aligned with the hollow interiors of the protrusion and barb; said barb, protrusion and barrel being in fluid communication so that fluid from the cartridge may flow to the needle, means for attaching the needle to the open end of the barrel; and
    a gripping feature located on the plunger, said gripping feature to engage the barb, whereby such engagement occurs when the plunger is fully compressed in the syringe body.

7. A syringe for use with a cartridge containing a liquid, the cartridge having a hollow body and being closed at one end with a piercable diaphragm and being closed at a second end with a plug, said diaphragm and said plug both creating a hermetic seal with said hollow body, the syringe assembly comprising:
    a syringe body having a hollow interior, an open proximal end and an oppositely spaced open distal end, and a means for removably receiving the cartridge, said cartridge receiving means comprising an elongated, exposed, longitudinal slot extending coaxially relative to and inwardly of the syringe body, said slot being located between the open proximal end and the oppositely spaced open distal end of said syringe body;
    a plunger slidably received by the syringe body at the proximal end;
    a barrel slidably received in the hollow interior at the distal end of the syringe body, said barrel comprising a hollow interior, a first open end and a second open end, said second open end comprises a protrusion to pierce the diaphragm of the cartridge;
    a sealing means in communication with the barrel and the syringe body;
    a hollow needle coupled to the open end of the barrel;
    means for retracting the needle inside the syringe body, said means comprising:
    a barbed member carried by the protrusion, said protrusion and said barbed member having concentric hollow interiors;

and wherein said barrel further comprises a concentric bore and distal aperture, said bore and aperture being aligned with the hollow interiors of the protrusion and barb; said barb, protrusion and barrel being in fluid communication so that fluid from the cartridge may flow to the needle, said needle being attached by a means to the open end of the barrel;

a gripping feature located on the plunger, said gripping feature to engage the barb, whereby such engagement occurs when the plunger is fully compressed in the syringe body; and a needle coupled to the open end of the barrel.

8. A syringe for use with a cartridge containing a liquid, the cartridge having a hollow body and being closed at one end with a piercable diaphragm and being closed at a second end with a plug, said diaphragm and said plug both creating a hermetic seal with said hollow body, the syringe assembly comprising:

a syringe body having a hollow interior, an open proximal end and an oppositely spaced open distal end, and a means for removably receiving the cartridge; said cartridge receiving means comprising an elongated, exposed, longitudinal slot extending coaxially relative to and inwardly of the syringe body, said slot being located between the open proximal end and the oppositely spaced open distal end of said syringe body;

a plunger slidably received by the syringe body at the proximal end;

a barrel slidably received in the hollow interior at the distal end of the syringe body, said barrel comprising a hollow interior, a first open end and a second open end, said second open end comprising a protrusion to pierce the diaphragm of the cartridge;

a sealing means in communication with the barrel and the syringe body;

a needle coupled to the open end of the barrel;

means for retracting the needle inside the syringe body, said means comprising:

a barbed member carried by the protrusion, said protrusion and said barbed member having concentric hollow interiors;

and wherein said barrel further comprises a concentric bore and distal aperture, said bore and aperture being aligned with the hollow interiors of the protrusion and barb; said barb, protrusion and barrel being in fluid communication so that fluid from the cartridge may flow to the needle, said needle being attached by a means to the open end of the barrel; and a gripping feature located on the plunger, said gripping feature to engage the barb, whereby such engagement occurs when the plunger is fully compressed in the syringe body.

9. A syringe assembly as claimed in claim 8 wherein the syringe body further comprises a finger rest and a handle adjacent to said finger rest, said finger rest being adjacent to the proximal end.

10. A syringe assembly as claimed in claim 8 wherein the plunger further comprises a looped member.

11. A syringe for use with a cartridge containing a liquid, the cartridge having a hollow body and being closed at one end with a piercable diaphragm and being closed at a second end with a plug, said diaphragm and said plug both creating a hermetic seal with said hollow body, the syringe assembly comprising:

a syringe body comprising a generally cylindrical tube having a hollow interior, an open proximal end and an oppositely spaced open distal end, and a longitudinal opening;

a plunger slidably received by the syringe body at the proximal end;

a barrel slidably received in the hollow interior at the distal end of the syringe body, said barrel comprising a hollow interior, an open end and an oppositely positioned protrusion, said protrusion to pierce the diaphragm of the cartridge;

a sealing means in communication with the barrel and the syringe body;

a needle coupled to the open end of the barrel; and a means for retracting the needle inside the body, said means comprising:

a barbed member carried by the protrusion, said protrusion and said barbed member having concentric hollow interiors;

and wherein said barrel further comprises a concentric bore and distal aperture, said bore and aperture being aligned with the hollow interiors of the protrusion and barb; said barb, protrusion and barrel being in fluid communication so that fluid from the cartridge may flow to the needle, said needle being attached by a means to a distal end of the barrel; and a gripping feature located on the plunger, said gripping feature to engage the barb, whereby such engagement occurs when the plunger is fully compressed in the syringe body.

12. A syringe assembly as claimed in claim 11 wherein the syringe body further comprises a finger rest and a handle adjacent to said finger rest, said finger rest being adjacent to the proximal end.

13. A syringe assembly as claimed in claim 11 wherein the plunger further comprises a looped member.

14. A syringe as claimed in claim 11 wherein the plunger further comprises a means for providing a breakaway feature.

15. The syringe assembly as claimed in claim 14 wherein the means for providing a breakaway feature includes a line of weakness at a predetermined location on the plunger.

* * * * *

UNITED STATES PATENT AND TRADEMARK OFFICE
CERTIFICATE OF CORRECTION

PATENT NO. : 6,808,511 B2
DATED : October 26, 2004
INVENTOR(S) : Gary J. Pond

It is certified that error appears in the above-identified patent and that said Letters Patent is hereby corrected as shown below:

Column 7,
Line 32, after "with a" delete "piercable" and substitute -- pierceable --.

Column 8,
Lines 3 and 41, after "with a" delete "piercable" and substitute -- pierceable --.

Column 9,
Line 15, after "with a" delete "piercable" and substiture -- pierceable --.

Colulmn 10,
Line 7, after "with a" delete "piercable" and substitute -- pierceable --.

Signed and Sealed this

Twenty-sixth Day of April, 2005

JON W. DUDAS
*Director of the United States Patent and Trademark Office*